(12) United States Patent
Wyckoff et al.

(10) Patent No.: US 10,206,667 B2
(45) Date of Patent: Feb. 19, 2019

(54) LAPAROSCOPIC TISSUE REMOVAL SYSTEM

(71) Applicant: University of Florida Research Foundation, Inc., Gainesville, FL (US)

(72) Inventors: Erich T. Wyckoff, Gainesville, FL (US); Daniel J. Gibson, Gainesville, FL (US); Christopher D. Batich, Gainesville, FL (US); Gregory Scott Schultz, Gainesville, FL (US)

(73) Assignee: University of Florida Research Foundation, Gainesville, FL (US)

( * ) Notice: Subject to any disclaimer, the term of this patent is extended or adjusted under 35 U.S.C. 154(b) by 0 days.

(21) Appl. No.: 15/745,015

(22) PCT Filed: Jul. 14, 2016

(86) PCT No.: PCT/US2016/042260
§ 371 (c)(1),
(2) Date: Jan. 15, 2018

(87) PCT Pub. No.: WO2017/011648
PCT Pub. Date: Jan. 19, 2017

(65) Prior Publication Data
US 2018/0206831 A1 Jul. 26, 2018

Related U.S. Application Data

(60) Provisional application No. 62/192,388, filed on Jul. 14, 2015.

(51) Int. Cl.
*A61B 17/00* (2006.01)
*A61B 17/29* (2006.01)
(Continued)

(52) U.S. Cl.
CPC ...... *A61B 17/00234* (2013.01); *A61B 17/221* (2013.01); *A61B 17/29* (2013.01);
(Continued)

(58) Field of Classification Search
CPC . A61B 17/00234; A61B 17/221; A61B 17/29; A61B 46/13; A61B 2090/064;
(Continued)

(56) References Cited

U.S. PATENT DOCUMENTS 5,611,803 A 3/1997 Heaven et al.
5,630,822 A * 5/1997 Hermann ......... A61B 17/00234
606/114

(Continued)

FOREIGN PATENT DOCUMENTS

EP 2598018 A1 6/2013
WO 199809569 A1 3/1998
(Continued)

OTHER PUBLICATIONS

International Search Report and Written Opinion for PCT/US16/042260 dated Oct. 7, 2016.

*Primary Examiner* — Eric Rosen
*Assistant Examiner* — Mikail Mannan
(74) *Attorney, Agent, or Firm* — Thomas | Horstemeyer, LLP (57) ABSTRACT

Provided herein are laparoscopic tissue removal systems, components, and uses thereof.

10 Claims, 9 Drawing Sheets

(51) Int. Cl.
*A61B 46/13* (2016.01)
*A61B 17/221* (2006.01)
*A61B 90/00* (2016.01)

(52) U.S. Cl.
CPC .... *A61B 46/13* (2016.02); *A61B 2017/00287* (2013.01); *A61B 2090/064* (2016.02)

(58) Field of Classification Search
CPC .......... A61B 17/22; A61B 2017/00287; A61B 2017/2215; A61B 17/22031; A61B 17/225; A61B 17/2251; A61B 2017/22035; A61B 2050/314; A61B 2050/316; A61B 2050/318; A61B 5/150366; A61F 2/82; A61F 2/95; A61J 1/10; A61J 1/12; A61M 1/0209
See application file for complete search history.

(56) References Cited

U.S. PATENT DOCUMENTS

| | | | |
|---|---|---|---|
| 6,383,195 B1 * | 5/2002 | Richard | ............... A61B 17/221 606/114 |
| 6,508,773 B2 | 1/2003 | Burbank et al. | |
| 7,547,310 B2 | 6/2009 | Whitfield | |
| 2010/0217299 A1 | 8/2010 | Williams et al. | |
| 2011/0087235 A1 | 4/2011 | Taylor et al. | |
| 2012/0277758 A1 | 11/2012 | Davis et al. | |

FOREIGN PATENT DOCUMENTS

| | | |
|---|---|---|
| WO | 2009048400 A1 | 4/2009 |
| WO | 2013075103 A1 | 5/2013 |

\* cited by examiner

LAPAROSCOPIC TISSUE REMOVAL SYSTEM

CROSS-REFERENCE TO RELATED APPLICATIONS

This application is the 35 U.S.C. § 371 national stage application of PCT Application No. PCT/US2016/042260, filed 14 Jul. 2016, where the PCT claims the benefit of and priority to U.S. Provisional patent application Ser. No. 62/192,388, filed on Jul. 14, 2015, entitled "LAPAROSCOPIC TISSUE REMOVAL SYSTEM," both of which are herein incorporated by reference in their entireties.

BACKGROUND

Laparoscopic procedures have greatly improved surgical procedures and patient recovery time. During some procedures it is important to prevent the loss of any tissue being removed during the procedure. As such, there exists a need for improved laparoscopic systems and procedures to reduce the risk of tissue loss during tissue removal.

SUMMARY

Provided herein are laparoscopic tissue removal systems that can contain a laparoscopic tissue manipulation device that can include an elongated member, the elongated member having a first end and a second end, where the first end can be configured to manipulate a bodily tissue; an adaptive sleeve that can contain an elongated cannula having a length longer than its width, the elongated cannula having a distal end and a proximal end, the distal end and comprising a first opening, the proximal end having a second opening, and the elongated cannula can be configured to receive the laparoscopic tissue manipulation device within its cavity; a first and a second containment ridge that can be circumferentially disposed on the outer surface of the elongated cannula, where the first and the second containment ridge can be separated from each other by a distance; and a containment device that can include a containment reservoir, which can contain at least two layers, where the innermost layer has longitudinal flexible ridges; an indicator, where the indicator can be contained between two layers of the containment reservoir; one or more ties that can be operatively coupled to the containment reservoir; and a hydraulic cinch, where the hydraulic cinch can have a pressure-responsive opening in the middle of the hydraulic cinch, where the pressure-responsive opening can be configured to receive the adaptive sleeve, and where the one or more ties can be slidably coupled to the pressure-responsive opening. The elongated member further includes a joint along its length, where the joint is configured to articulate the first end in one or more directions. The distance separating the first containment ridge and the second containment ridge can be configured to secure the hydraulic cinch when the elongated cannula is positioned through the pressure-responsive opening. The elongated member can further contain a grasper at one end. One end of the elongated member can be configured to mince a tissue portion. The elongated cannula can have a 12 mm or a 15 mm cavity diameter. The indicator can be a fluorescent compound. The indicator can be contained between the innermost layer and another layer of the containment reservoir. The containment reservoir can further contain a pressure sensor operatively coupled to a layer of the containment reservoir.

Also provided herein are containment devices that can contain a containment reservoir having at least two layers, where the innermost layer can have longitudinal flexible ridges; an indicator, where the indicator can be contained between two layers of the containment reservoir; one or more tie strings that can be operatively coupled to the containment reservoir; and a hydraulic cinch, where the hydraulic cinch has a pressure-responsive opening, where the pressure-responsive opening can be configured to receive the adaptive sleeve, and where the one or more tie strings can be slidably coupled to the pressure-responsive opening. The containment reservoir can further include a pressure sensor operatively coupled to a layer of the containment reservoir. The indicator can be a fluorescent compound. The indicator can be contained between the innermost layer and another layer of the containment reservoir. The containment reservoir can be collapsible. The containment reservoir can have a length longer than its diameter.

Also provided herein are methods that can include the step of: removing a tissue sample from a subject using a laparoscopic tissue removal system as described herein.

Also provided herein are methods that can contain the step of: manipulating a tissue sample obtained from a subject, where manipulation occurs within the body of the subject, and where manipulation occurs within a containment reservoir as provided herein. The manipulating can be mincing.

BRIEF DESCRIPTION OF THE DRAWINGS

Further aspects of the present disclosure will be readily appreciated upon review of the detailed description of its various embodiments, described below, when taken in conjunction with the accompanying drawings.

FIG. 9 shows a cartoon demonstrating one embodiment of the laparoscopic tissue removal system in use to contain and manipulate a tissue fragment contained within the containment reservoir. As shown in FIG. 9, the containment reservoir can be cinched with a hydraulic cinch inside of a body cavity.

FIG. 10 shows a cartoon demonstrating one embodiment of the laparoscopic tissue removal system in use to contain and manipulate a tissue fragment contained within the containment reservoir. As shown in FIG. 10, the containment reservoir can be cinched with the hydraulic cinch outside of the body cavity.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of the mechanical arts, surgical arts and the like, which are within the skill of the art. Such techniques are explained fully in the literature.

Discussion

Endocatch surgical bags are currently used to remove tissue masses from body cavities, such as the abdomen. Fluid filled cysts can often be drained while inside an endocatch bag during a surgical procedure. After the tissues have been placed in the endocatch bags and optionally drained and/or minced (i.e. manipulated into many smaller pieces) where necessary, the endocatch bag and its contents can be removed from the body cavity. More often than not, masses of concern are either solid or solid-cystic. These masses are of concern because of they are potentially malignant. As such, spillage of any contents of these masses into the body cavity during tissue removal could be detrimental to the patient.

With that said, described herein are embodiments of a laparoscopic tissue removal system that can include a containment device, an adaptive sleeve, and a laparoscopic tissue manipulation device. The laparoscopic tissue removal system or any of the devices described herein can be used during a minimally invasive surgical procedure. The piece of tissue removed during a minimally invasive surgical procedure can be contained and optionally minced within a containment reservoir of the containment device. The containment reservoir can be configured and/or operatively coupled to the adaptive sleeve to prevent spillage of the tissue contained within the containment reservoir during removal and optional mincing of the tissue. The devices and systems described herein can eliminate the need for a large incision to remove an intact tissue, including tumors, while reducing the risk to patients of tissue (or tumor) spillage into the patient.

Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Figure 1:
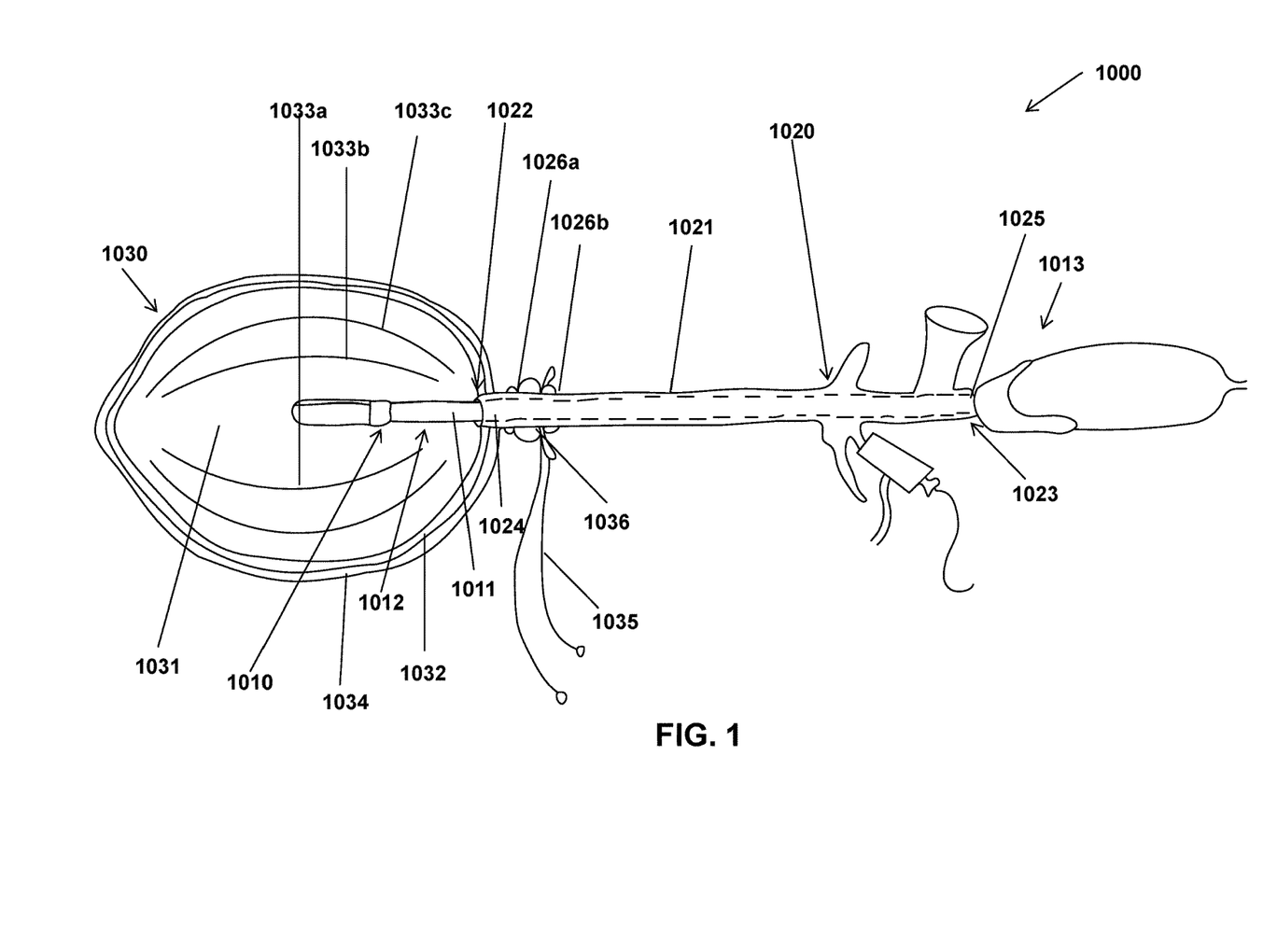
FIG. 1 shows one embodiment of a laparoscopic tissue removal system.

With the general concept of the laparoscopic tissue removal system in mind, attention is directed to FIG. 1, which shows one embodiment of a laparoscopic tissue removal system 1000. The laparoscopic tissue removal system can contain a laparoscopic tissue manipulation device 1010. The laparoscopic tissue manipulation device 1010 can have an elongated member 1011 having a length longer than its width. The elongated member can have a first end 1012 and a second end 1013. The first end 1012 can be configured to manipulate a bodily tissue. As used in this context, "manipulate" refers to handling, mincing, grabbing, squeezing, draining, aspirating, cutting, or otherwise physically interacting with a tissue portion.

The laparoscopic tissue removal system 1000 can further contain an adaptive sleeve 1020 configured to receive the laparoscopic tissue manipulation device 1010. The adaptive sleeve 1020 can have an elongated cannula 1021 having a length longer than its width. The elongated cannula 1021 can have a distal end 1022, which can enter the subject during use, and a proximal end 1023, which is farthest from the subject during use. The distal end 1022 has a first opening 1024 and the proximal end has a second opening 1025.

The adaptive sleeve 1020 can further contain at least two containment ridges 1026a, b (collectively 1026) that can be disposed on, integrated with, operatively coupled to, or otherwise attached to the outer surface of the elongated cannula 1021 of the adaptive sleeve 1020. The containment ridges 1026 can be separated from one another by a distance. The distance that separates the containment ridges 1026 is such that a containment reservoir can be securely coupled to the adaptive sleeve 1020. This is discussed in detail elsewhere herein.

The laparoscopic tissue removal system 1000 can further contain a containment device 1030 that is configured to contain a tissue sample. The containment device 1030 can include a containment reservoir 1031 having at least two layers. In some embodiments, innermost layer 1032 (i.e. the layer that is the lining of the cavity of the containment reservoir) can contain flexible longitudinal ridges 1033 *a,b,c* . . . (collectively 1033) that can project into the interior of the containment reservoir 1031. In other embodiments, the flexible longitudinal ridges can be part of an outer layer 1034 (i.e. a layer that is disposed, either directly or indirectly, about, operatively coupled to, bonded, laminated, or otherwise attached to the side of the innermost layer 1032 opposite of the cavity of the containment reservoir 1031). The containment reservoir 1031 can contain an indicator. The indicator can be contained between two layers (e.g. the innermost layer 1032 and an outer layer 1034) of the containment reservoir 1031. The indicator can be such that it alerts the user that the integrity of the containment reservoir 1031, or a layer thereof, has been compromised. The containment reservoir 1031 can contain an opening at one end that is configured to fit over an end of the adaptive sleeve 1020.

The containment device 1030 can further have one or more ties 1035 that can be operatively coupled to the containment reservoir 1031. In some embodiments, the ties 1035 can be operatively coupled to the end of the containment reservoir 1031 having the opening. The containment device 1030 can further contain a hydraulic cinch 1036. The hydraulic cinch 1036 can have a pressure-responsive opening that is configured to receive the adaptive sleeve 1020. The tie(s) 1035 can be slidably coupled to the pressure responsive opening of the hydraulic cinch 1036. During use, the hydraulic cinch 1036 can be positioned between two containment ridges 1026 on the elongated cannula 1021. In this way the containment device 1030 can be secured to the adaptive sleeve 1020 of the laparoscopic tissue removal device 1000.

Figure 2:
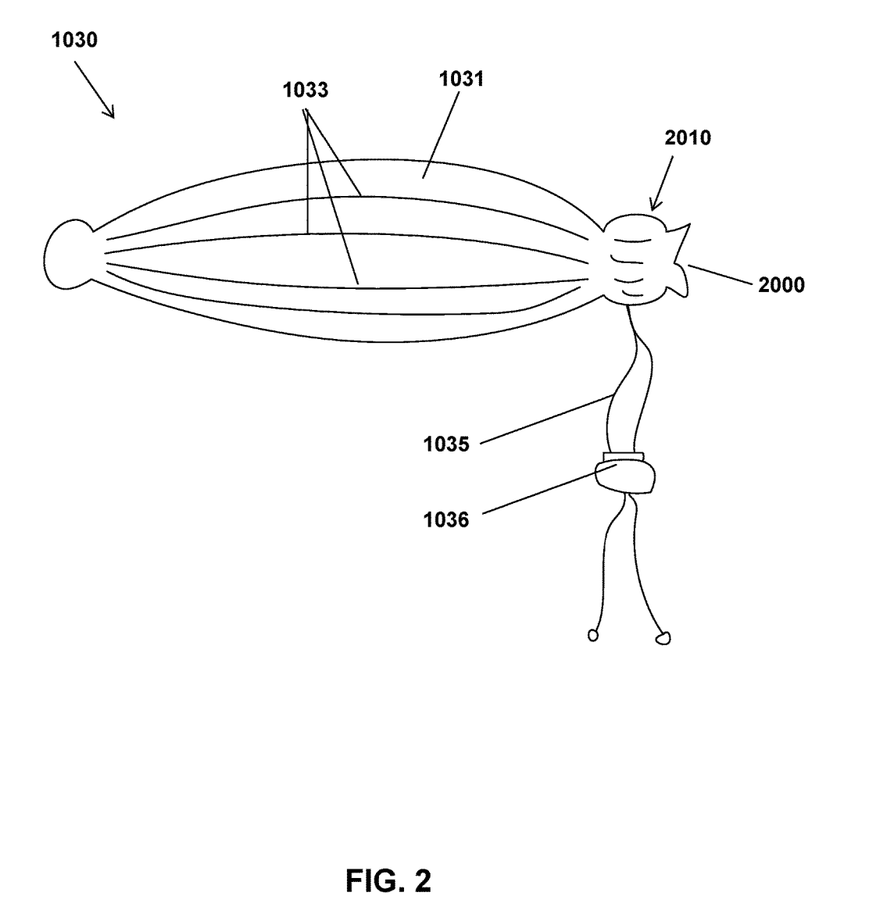
FIG. 2 shows one embodiment of a containment device that can be part of the laparoscopic tissue removal system of FIG. 1.

With the discussion of FIG. 1 in mind, attention is directed to FIG. 2, shows one embodiment of a containment device 1030 that can be part of the laparoscopic tissue removal system 1000 of FIG. 1. As previously described, the containment device 1030 can include a containment reservoir 1031 having at least two layers. The containment reservoir 1031 can be flexible and collapsible. The containment reservoir 1031 can have a length longer than its diameter or width. In some embodiments, innermost layer 1032 can contain flexible longitudinal ridges 1033 that can project into the interior of the containment reservoir 1031. In other embodiments, the flexible longitudinal ridges can be part of an outer layer 1034. The layers 1032, 1034 can be flexible and can be made out of a suitable material. In some embodiments, the layers are each made from the same suitable material. In other embodiments, at least one layer is made from a different suitable material that at least one other layer. Suitable materials for the layers include, but are not limited to, synthetic and natural compounds, polymers, and composites thereof (e.g. rubber, polypropylene, nylon, plastics, polyurethane, silicone, etc.), natural and synthetic fibrous materials (such as cotton), metal fibers and composite materials containing metal fibers, and Kevlar. The suitable material can be rip-stop. The suitable material can be biocompatible, resistant to tearing, cutting, and/or heating, translucent, opaque, or semi-translucent, and/or flexible.

The containment reservoir 1031 can contain an indicator. The indicator can be contained between two layers (e.g. the innermost layer 1032 and an outer layer 1034) of the containment reservoir 1031. The indicator can be such that it alerts the user that the integrity of the containment reservoir 1031, or a layer thereof, has been compromised. By providing a visual signal to the user (e.g. doctor), the indicator can provide an additional layer of protection for the patient undergoing a tissue removal procedure. The indicator can be such that it produces an alert (color change, a light or other visual signal) when exposed to the air or a fluid (e.g. a bodily fluid or other fluid contained within the containment reservoir 1031 during use, such as saline). For example, the indicator can be a fluorescent compound that fluoresces when exposed to the air or a fluid. In other embodiments, the indicator can be a pH sensitive substance that changes color upon a change in pH, which would occur when the substance comes in contact with a fluid, such as a bodily fluid or other fluid introduced to the device or body during a tissue removal procedure.

The containment reservoir 1031 can also include a pressure sensor operatively coupled or otherwise attached to a layer of the containment reservoir 1031. The inclusion of a pressure sensor in the containment reservoir 1031 can help alert a user that the containment reservoir is distended too much, and as such, one or more layers of the containment reservoir 1031 is at risk of breaking or tearing.

The containment reservoir 1031 can contain an opening 2000 at one end that is configured to fit over an end of the adaptive sleeve 1020. As previously described, containment device 1030 can further have one or more ties 1035 that can be operatively coupled to the containment reservoir 1031. In some embodiments, the ties 1035 can be operatively coupled to the end of the containment reservoir 1031 having the opening 2000.

The containment device 1030 can further contain a hydraulic cinch 1036. The hydraulic cinch 1036 can have a pressure-responsive opening that is configured to receive the adaptive sleeve 1020. In some embodiments, the hydraulic cinch 1036 can be a fluid filled ring or bulb with a pressure-responsive opening in the middle of the ring. In some embodiments the hydraulic cinch 1036 has a diameter in the closed state of 2.0 cm or less. In some embodiments, the hydraulic cinch 1036 has a diameter in the closed state of about 1.5-1.0 cm. The tie(s) 1035 can be slidably coupled to the pressure-responsive opening of the hydraulic cinch 1036. The pressure-responsive opening mechanism is discussed in further detail with respect to FIGS. 4A-4B. The hydraulic cinch can contain interlocking teeth that can grip the tie(s) 1035 to lock the hydraulic cinch 1036 in place at a position along tie(s) 1035. The interlocking teeth can be configured to have a ratchet action, and as such, only release the tie(s) 1035 when the tie(s) are pulled through the hydraulic cinch 1036 in one direction or when the teeth are otherwise acted upon to cause their release of the tie(s) 1035, such as by an actuator or pressure applied to the hydraulic cinch (see e.g. FIGS. 4A-4B). In some embodiments, the tie(s) 1035 can be operatively coupled to the containment reservoir 1031 in a drawstring mechanism, where the tie(s) 1035 can be operatively coupled to the portion 2010 of the containment reservoir 1031 encircling the opening 2000.

Figure 3:
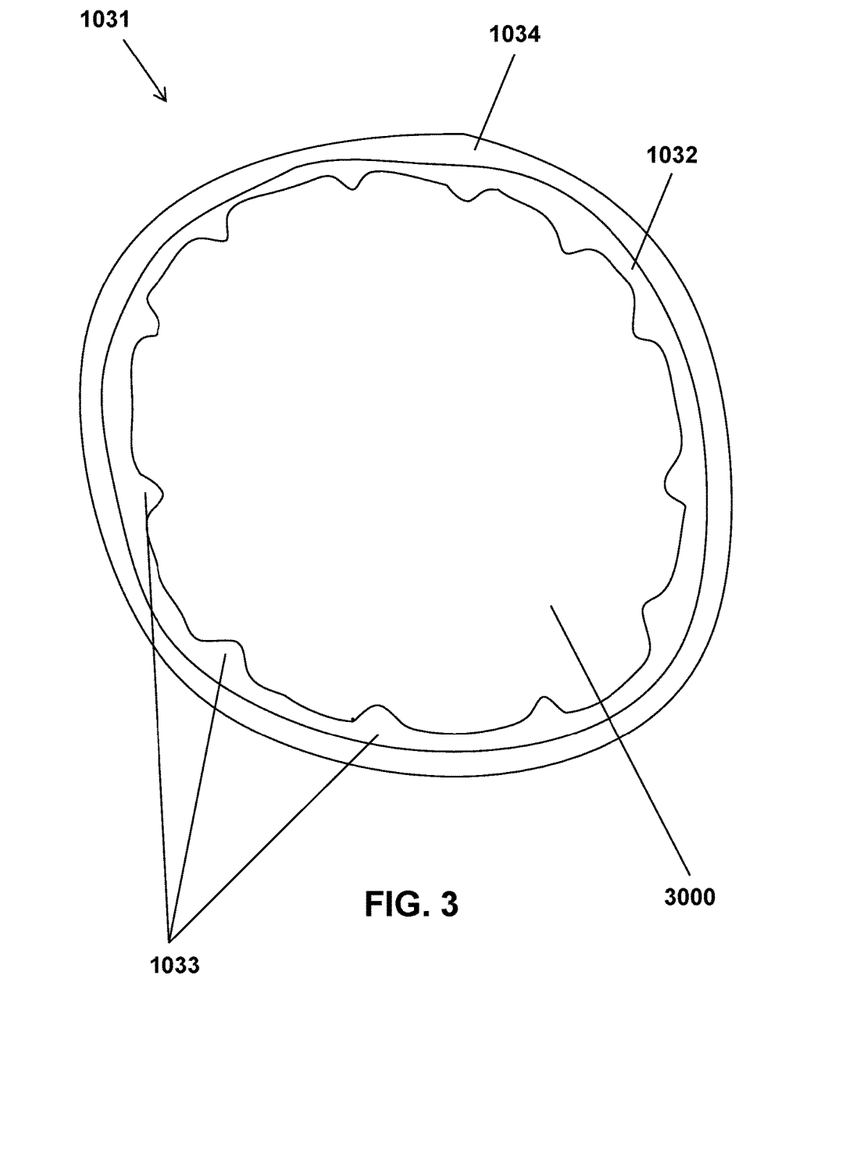
FIG. 3 shows a cross-section of one embodiment of a containment reservoir that can be part of the containment device of FIG. 2.

A discussion of aspects of the containment reservoir 1031 continues with FIG. 3, which shows a cross-section of one embodiment of a containment reservoir that can be part of the containment device of FIG. 2. As shown in FIG. 3, the containment reservoir 1031 can contain an innermost layer 1032 and at least one outer layer 1034. The innermost layer 1032 can have longitudinal flexible ridges 1033 that can be circumferentially placed at various intervals around the innermost layer 1032. The flexible ridges can be configured to protrude a distance into the cavity 3000 of the containment reservoir 1031. The flexible ridges can be assist in preventing undesired collapse of the containment reservoir 1031, facilitate closure of the containment reservoir 1031, and assist with stabilization of the tissue portion removed during a tissue removal procedure.

Figure 4A:
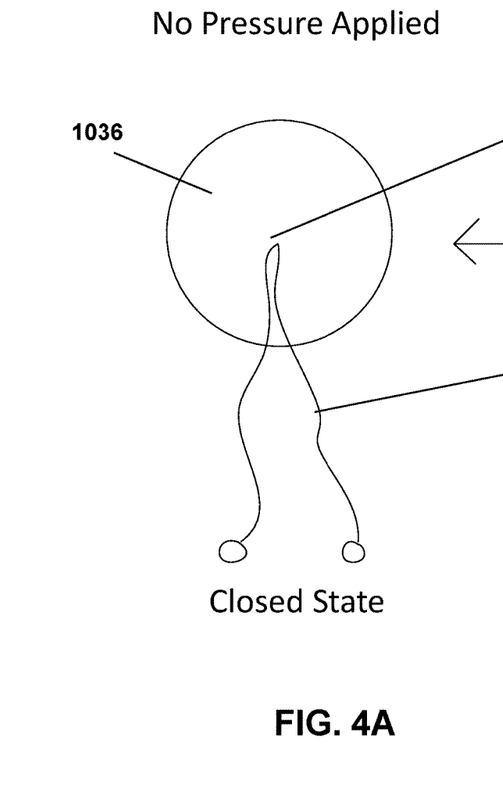
FIGS. 4A-4B show the closed state (FIG. 4A) and the open state (FIG. 4B) of one embodiment a hydraulic cinch of the containment device of FIG. 2.
Figure 4B:
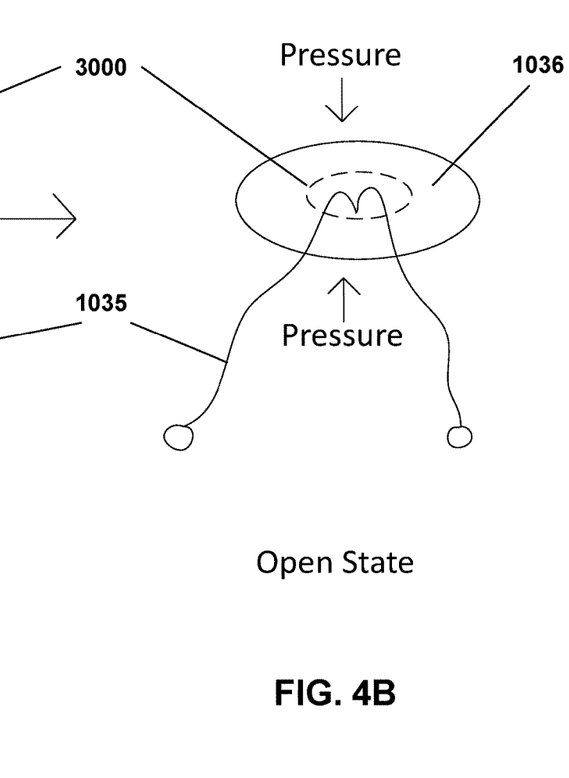

Attention is next directed to FIGS. 4A and 4B, which show the closed state (FIG. 4A) and the open state (FIG. 4B) of one embodiment a hydraulic cinch of the containment device of FIG. 2. As previously described, the hydraulic cinch 1036 contains a pressure-responsive opening 3000. As such, can exist in a closed state (FIG. 4A) when no pressure is applied to the outer edges of the hydraulic cinch 1036 or in an open state (FIG. 4B) when pressure is applied to the outer edges of the hydraulic cinch 1036. Pressure can be applied to the hydraulic cinch 1036, for example, by a grasper tool operated by a user. When in the closed state, the tie(s) 1035 (or other device (e.g. the adaptable sleeve 1020) are prevented from sliding though the pressure-responsive opening 3000. In some embodiments, during use an end of the containment reservoir 1031 can be passed through the pressure-responsive opening 3000 when the hydraulic cinch 1036 is manipulated into the open state, such that when the hydraulic cinch 1036 is allowed to return to the closed state, the containment reservoir is secured shut. This offers a closing mechanism in addition to the tie(s) 1035 to further ensure that the containment reservoir is securely closed. Due to the pressure-responsive configuration of the hydraulic cinch 1036, when the hydraulic cinch 1036 is disposed about the adaptive sleeve 1020, the hydraulic cinch 1036 creates a pressure seal of the containment reservoir 1031 at the end with the opening and helps prevent spillage of the bag contents into the body cavity of a subject during use.

Figure 5:
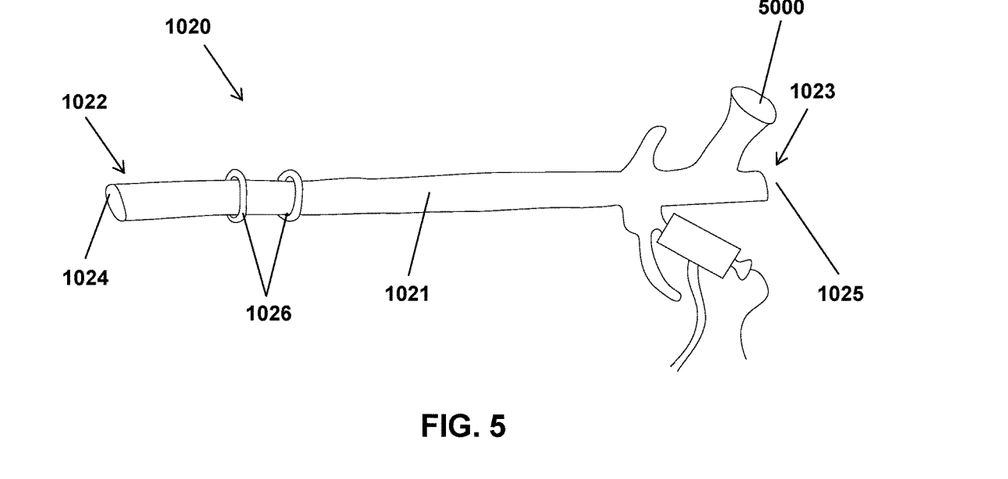
FIG. 5 shows one embodiment of an adaptive sleeve that can be part of the laparoscopic tissue removal system of FIG. 1.

Attention is now turned to FIG. 5, shows one embodiment of an adaptive sleeve 1020 that can be part of the laparoscopic tissue removal system of FIG. 1. As previously described, the adaptive sleeve 1020 can be configured to receive the laparoscopic tissue manipulation device 1010. The adaptive sleeve 1020 can have an elongated cannula 1021 having a length longer than its width. The wall of the elongated cannula 1021 can have any suitable desirable width. In some embodiments, the wall of the elongated cannula can be 0.0001 mm to about 100 mm thick. One of skill in the art will appreciate a suitable cannula wall width. The elongated cannula 1021 can have any suitable desired length. In some embodiments, the length of the elongated cannula 1021 can be from about 1 mm to about 1000 mm. One of skill in the art will appreciate that the length and width of the elongated cannula 1021 can be varied according to, inter alia, the patient size, the region from which the tissue is to be removed from, etc.

The elongated cannula 1021 can have any cross-sectional shape, including but not limited to round, elliptical, square, hexagonal, rectangular, or triangular. One of skill in the art will appreciate other suitable cross-sectional shapes. Further, the cavity of the elongated cannula 1021 can have any cross-sectional shape, including but not limited to round, elliptical, square, hexagonal, rectangular, or triangular. One of skill in the art will appreciate other suitable cross-sectional shapes. The cross-sectional shape of the elongated cannula 1021 and the cavity of the elongated cannula can be the same or different from one another. The elongated cannula 1021 can have a width (or diameter) of about 0.001 mm to about 100 mm. The cavity of the elongated cannula can be configured to receive the elongated member 1011. The cavity of the elongated cannula can have a width (or diameter) of about 0.001 mm to about 100 mm. In other words, the opening at either or both ends of the adaptive sleeve can have a width (or diameter) of about 0.001 mm to about 100 mm.

As previously described in relation to FIG. 1, the adaptive sleeve 1020 can have a distal end 1022 and a proximal end 1023 with each end having an opening (1024,1025). The distal end 1022 can be tapered. In other words, the width (or diameter) of the elongated cannula can be decreased along the length of a portion of distal end of 1022 of the elongated cannula 1021. In some embodiments, this can result in a first opening 1024 that has a width (or diameter) that is less than the width (or diameter) of the cavity of the elongated cannula 1021 at another point along the length of the elongated cannula 1021. Similarly, the proximal end 1023 can be tapered. The distal end 1022 and/or the proximal end 1023 can be flush (or flat), beveled to any degree, or any other shape as desired by one of skill in the art. When beveled, the distal end 1022 and/or the proximal end 1023 can form a pointed tip or a rounded tip.

As previously described, the adaptive sleeve can contain at least two containment ridges 1026 that can be disposed on, integrated with, operatively coupled to, or otherwise attached to the outer surface of the elongated cannula 1021 of the adaptive sleeve 1020. During use, the hydraulic cinch 1036 can be placed between two containment ridges 1026. The distance between the two containment ridges 1026 can be such that they each touch a side of the hydraulic cinch thereby preventing movement of the hydraulic cinch 1036 along the length of the elongated cannula 1021 of the adaptive sleeve 1020. The outer surface of the adaptive sleeve 1020 between two containment ridges 1026 can be coated or otherwise have a surface that further facilitates a seal between the containment reservoir 1031 and the adaptive sleeve 1020. In some embodiments, the coting or surface can contain a natural or synthetic polymer or polymer composite. The coating or surface can be, without limitation, a rubber, silicone, polyurethane or a combination thereof.

The proximal end 1023 of the adaptive sleeve 1020 can contain an optical imaging apparatus physically and optically coupled to the adaptive sleeve 1020 that allows the adaptive sleeve to also serve as a laparoscope to remove the need for additional surgical sites for a separate laparoscope. As such, such in some embodiments, the proximal end 1023 of the adaptive sleeve can include an eyepiece 5000. Other typical devices utilized during laparoscopic procedures can be incorporated into the adaptive sleeve 1020 as shown in FIG. 5 and as will be appreciated by those of ordinary skill in the art.

Figure 6:
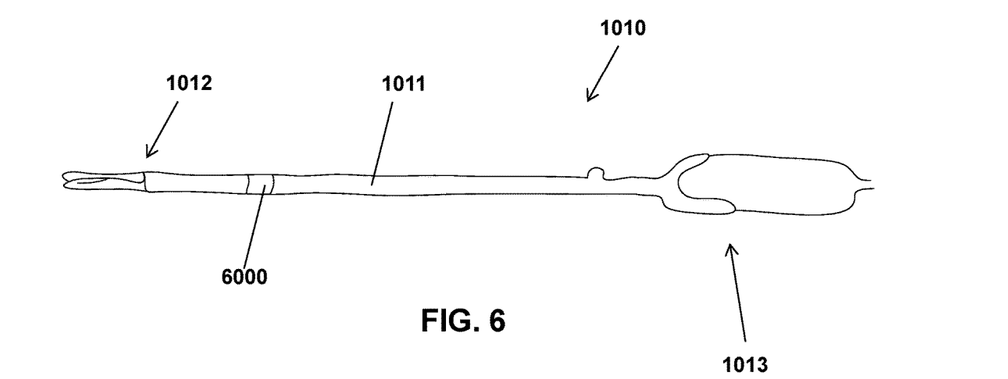
FIG. 6 shows one embodiment of a laparoscopic tissue manipulation device that can be part of the laparoscopic tissue removal system of FIG. 1.

Attention is now directed to FIG. 6, which shows one embodiment of a laparoscopic tissue manipulation device 1010 that can be part of the laparoscopic tissue removal system of FIG. 1. As previously described, the laparoscopic tissue manipulation device 1010 can have an elongated member 1011 having a length longer than its width. The elongated member 1011 can have any cross-sectional shape, including but not limited to round, elliptical, square, hexagonal, rectangular, or triangular. One of skill in the art will appreciate other suitable cross-sectional shapes. The elongated member 1011 can have a width (or diameter) of about 0.001 mm to about 100 mm. The elongated member 1011 can have any suitable desired length. In some embodiments, the length of the elongated member 1011 can be from about 1 mm to about 1000 mm. One of skill in the art will appreciate that the length and width can be varied according to, inter alia, the patient size, the region from which the tissue is to be removed from, etc. The first end 1012 can be configured to manipulate a bodily tissue. As used in this context, "manipulate" refers to handling, mincing, grabbing, squeezing, draining, aspirating, cutting, or otherwise physically interacting with a tissue portion.

Figure 7:
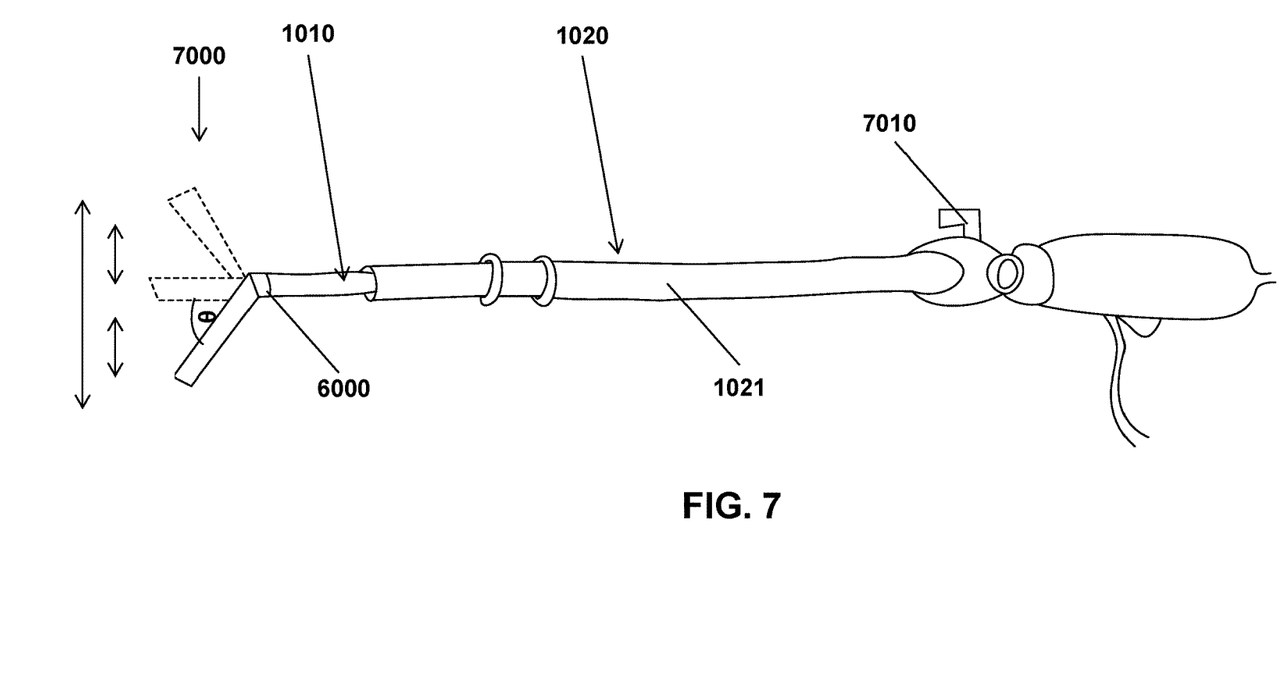
FIG. 7 shows one embodiment of the laparoscopic tissue manipulation device of FIG. 6 containing a joint and an articulable end, where the laparoscopic tissue manipulation tool is inserted through one embodiment of the adaptive sleeve of FIG. 5.

In some embodiments, the elongated member 1011 can have a joint 6000 positioned along its length that allows the elongated member 1011 to flex and/or articulate about the joint. The joint 6000 can be configured to allow articulation of the first (e.g. distal) end 1012 of the elongated member in any direction or combination of directions upon activation by a user. With that said, attention is directed to FIG. 7, which shows one embodiment of the laparoscopic tissue manipulation tool containing a joint 6000 and an articulable end 7000, where the laparoscopic tissue manipulation tool is inserted through one embodiment of the adaptive sleeve of FIG. 5. As shown in FIG. 7, the articulable end 7000 can pivot through the joint 6000. The user can activate articulation of the articulable end 7000 in some embodiments, via an articulation lever 7010 that can be operatively or physically coupled to the joint to facilitate articulation of the articulable end 7000. In some embodiments, the joint 6000 is configured such that θ is about 30° to about 45°. One of ordinary skill in the art will appreciate that the joint can be configured to articulate the articulable end at any desired degree and in one or more direction.

Figure 8:
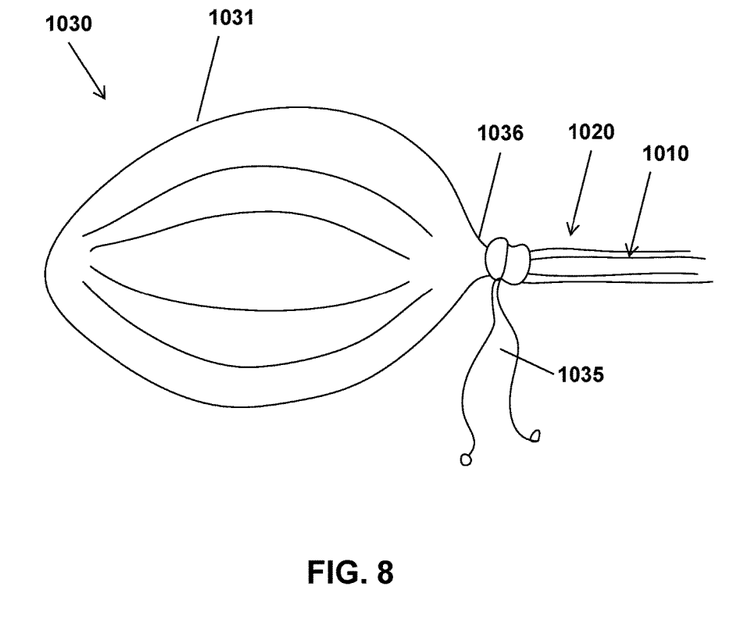
FIG. 8 shows one embodiment of the laparoscopic tissue removal system where the containment reservoir of the containment device is operatively coupled to the adaptive sleeve, where the containment reservoir is distended with a suitable fluid.
Figure 9:
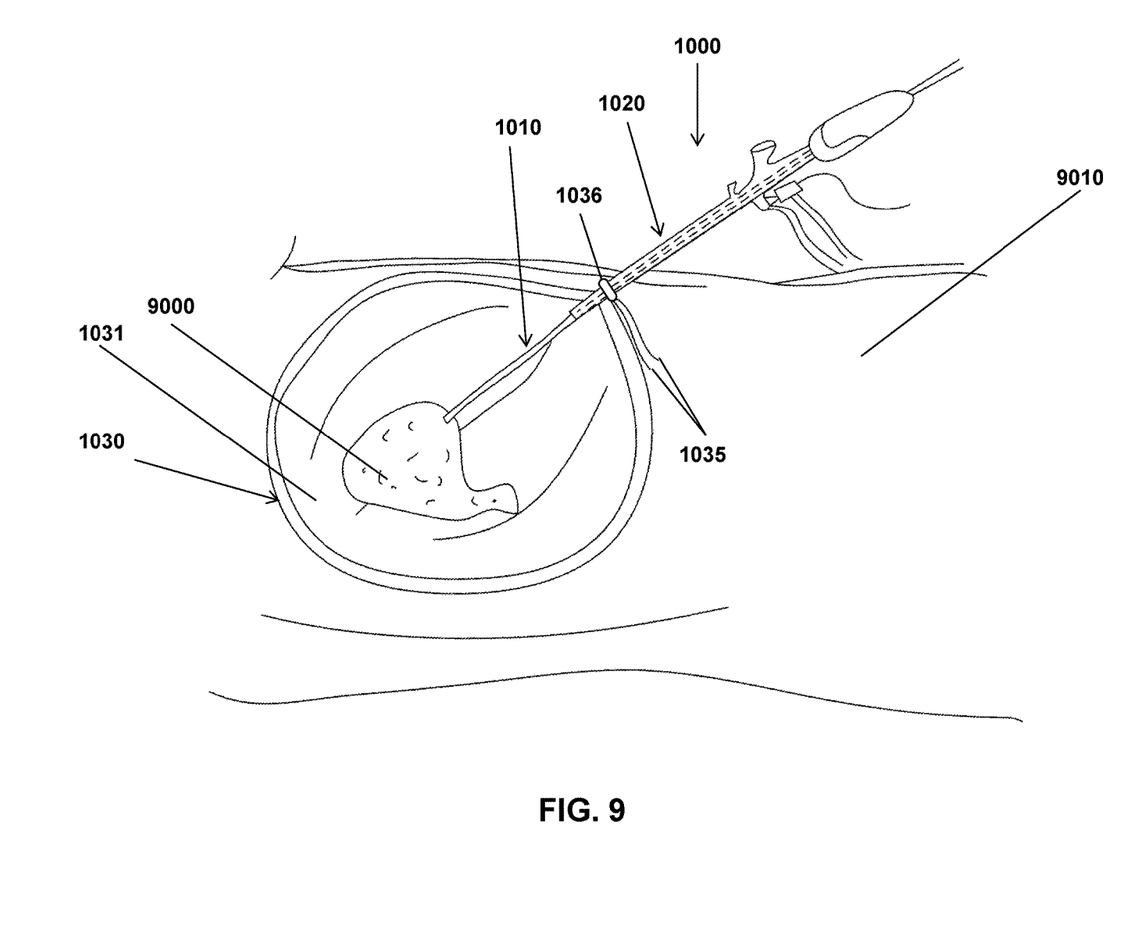

With the laparoscopic tissue removal system 1000 and components thereof described, attention is directed to FIGS. 8-9, which demonstrate the laparoscopic tissue removal system 1000 in use. Discussion begins with FIG. 8, which shows one embodiment of the laparoscopic tissue removal system where the containment reservoir 1031 of the containment device is operatively coupled to the adaptive sleeve 1020, where the containment reservoir 1031 is distended with a suitable fluid. The end of the containment reservoir 1031 with the opening can be passed through the hydraulic cinch 1036 and then the adaptive sleeve 1020 can be inserted into the containment reservoir 1036 through the opening (and thus also through the pressure-responsive opening of the hydraulic cinch 1036). The adaptive sleeve 1020 can be inserted into the containment reservoir 1031 far enough such that the end containment reservoir 1031 is over two containment ridges on the adaptive sleeve 1020. The hydraulic cinch 1036 can then be slid over the end of the containment reservoir 1031 by applying pressure to the hydraulic cinch 1036 (see FIGS. 4A-4B) until the hydraulic cinch 1036 is positioned between the two containment ridges. At that point, the pressure applied to the hydraulic cinch 1036 can be removed and the hydraulic cinch 1036 will clamp down around the adaptive sleeve 1020 and can secure the hydraulic clamp and the containment reservoir to the adaptive sleeve. A fluid, such as saline, can be pumped into the containment reservoir causing its distension. This can create a working space for the user to conduct tissue manipulation, such as mincing, in. The laparoscopic tissue manipulation device 1010 can be inserted into the adaptive sleeve and into the workable space created by the distended containment reservoir 1031.

FIG. 9 shows a cartoon demonstrating one embodiment of the laparoscopic tissue removal system 1000 in use to contain and manipulate a tissue fragment 9000 contained within the containment reservoir 1031 while inside a subject 9010. In some embodiments, after the tissue portion 9000 has been obtained and placed in the containment reservoir 1031, the containment reservoir 1031 can be operatively coupled to the adaptive sleeve 1020 as described in relation to FIG. 8. The containment reservoir 1031 can be distended as described in relation to FIG. 8 and the laparoscopic tissue manipulation device 1010 can be received by the adaptive sleeve 1020 and inserted into the workable space within the containment reservoir 1031. The laparoscopic tissue manipulation device 1010 can be operated by a user to manipulate the tissue portion 9000 prior to and to facilitate removal of the laparoscopic tissue removal system 1000 and tissue portion 9000 from the subject. In some embodiments, the tissue portion can be minced, cut, chopped, by physical means or by the use of energy (such as bipolar energy via a bipolar energy device) to separate the tissue into pieces. In some embodiments, the laparoscopic tissue removal device 1010 can be configured to perform one or more of these actions.

After the desired manipulation of the tissue portion 9000 is complete, in some embodiments, the tissue or pieces of tissue contained in the containment reservoir 1031 are removed from the containment reservoir 1031 prior to removal of the containment reservoir 1031 from the subject 9010. In these embodiments, the laparoscopic tissue manipulation device 1010 or other suitable device can be used to remove the tissue or portions thereof 9000 contained in the containment reservoir 1031 through the adaptive sleeve 1020. After removal of the tissue 9000, the containment reservoir can be collapsed and the laparoscopic tissue removal system 1000 can be removed from the subject 9000 using skills generally known to those in the art. In some embodiments, the tissue containment device 1030 can be removed from the adaptive sleeve 1020 prior to removal of the containment device 1030 and the adaptive sleeve 1020 from the subject 9010. The containment device 1030 can be removed through the same incision or trochar that the adaptive sleeve 1020 was introduced through. In other embodiments, the containment device 1030 can be removed through a different incision or trochar placed in the patient.

In other embodiments, the laparoscopic tissue manipulation device 1010 can be removed from the containment reservoir 1031 and adaptive sleeve 1020, the tie(s) 1035 can be pulled tight to collapse and close off the containment reservoir 1031. The hydraulic cinch 1036 can be moved off the end of the adaptive sleeve 1020 by applying pressure to open the hydraulic cinch 1036. In some embodiments, the tie(s) 1035 are passed through the hydraulic cinch along with the end of the containment reservoir 1031 and optionally tied, thus completely releasing the closed containment reservoir 1031 from the adaptive sleeve while ensuring that the containment reservoir 1031 does not open to release its contents into the subject. The pressure on the hydraulic cinch 1036 can be released thus leaving the hydraulic cinch coupled to the adaptive sleeve or otherwise ready for removal from the subject. The containment reservoir 1031 can then be removed from the patient. In some embodiments, the containment reservoir 1031 and its contents can be removed through the adaptive sleeve 1020.

Figure 10:
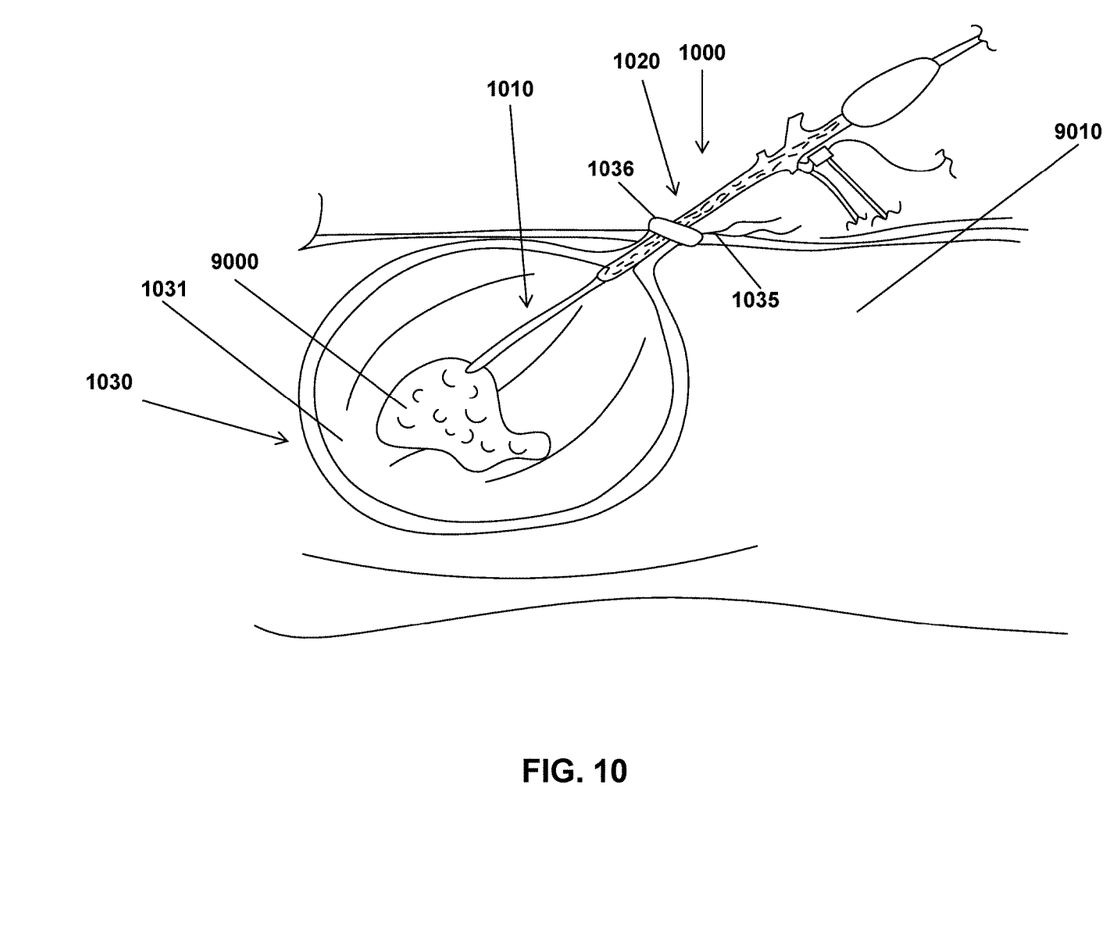

In some embodiments the hydraulic cinch 1036 can be moved onto the end of the containment reservoir 1031 by applying pressure to the hydraulic cinch 1036 and clamped down on the containment reservoir end with the opening by removing pressure to the hydraulic clamp 1036 to further secure the closure of the containment reservoir 1031 to help prevent spillage. The hydraulic cinch 1036 can then be removed along with the containment reservoir 1031 and its contents. In other embodiments, the hydraulic cinch 1036 can be moved to the end of the tie(s) 1035 and prevent opening of the containment reservoir 1031 by preventing loosening of the tie(s) 1035. As shown in FIG. 9, the containment reservoir can be cinched with the hydraulic cinch within a body cavity. As shown in FIG. 10, the containment reservoir can be cinched with the hydraulic cinch outside of the body cavity.

One of skill in the art will appreciate that the device described herein can be used in a variety of ways and the method of use can include a variety of sequence of events than those described herein. These variations on the method of use are within the spirit and scope of this disclosure.

We claim:

1. A laparoscopic tissue removal system comprising:
a laparoscopic tissue manipulation device comprising:
an elongated member, the elongated member having a first end and a second end, where the first end is configured to manipulate a bodily tissue;
an adaptive sleeve comprising:
an elongated cannula having a length longer than its width, the elongated cannula having a distal end and a proximal end, the distal end comprising a first opening, the proximal end comprising a second opening, and the elongated cannula being configured to receive the laparoscopic tissue manipulation device within its cavity;
a first and a second containment ridge circumferentially disposed on the outer surface of the elongated cannula, where the first and the second containment ridge are separated from each other by a distance; and
a containment device comprising:
a containment reservoir comprising:
at least two layers, where the innermost layer comprises longitudinal flexible ridges;
an indicator, where the indicator is contained between two layers of the containment reservoir;
one or more ties operatively coupled to the containment reservoir; and
a hydraulic cinch, where the hydraulic cinch comprises a fluid filled ring or bulb with a pressure-responsive opening in the middle of the hydraulic cinch, where the pressure-responsive opening is configured to receive the adaptive sleeve, and where the one or more ties are slidably coupled to the pressure-responsive opening.

2. The laparoscopic tissue removal system of claim 1, wherein the elongated member further comprises a joint along its length, where the joint is configured to articulate the first end in one or more directions.

3. The laparoscopic tissue removal system of claim 1, wherein the distance separating the first containment ridge and the second containment ridge is configured to secure the hydraulic cinch when the elongated cannula is positioned through the pressure-responsive opening.

4. The laparoscopic tissue removal system of claim 1, wherein the elongated member further comprises a grasper at one end.

5. The laparoscopic tissue removal system of claim 1, wherein one end of the elongated member is configured to mince a tissue portion.

6. The laparoscopic tissue removal system of claim 1, wherein the elongated cannula has a 12 mm or a 15 mm cavity diameter.

7. The laparoscopic tissue removal system of claim 1, wherein the indicator is a fluorescent compound.

8. The laparoscopic tissue removal system of claim 1, wherein the indicator is contained between the innermost layer and another layer of the containment reservoir.

9. The laparoscopic tissue removal system of claim 1, wherein the containment reservoir further comprises a pressure sensor operatively coupled to a layer of the containment reservoir.

10. A method comprising:
removing a tissue sample from a subject using a laparoscopic tissue removal system as in claim 1.

* * * * *